United States Patent [19]

Medri

[11] Patent Number: 4,789,546
[45] Date of Patent: Dec. 6, 1988

[54] MULTIPLE-LAYER TABLET WITH CONTRASTING ORGANOLEPTIC CHARACTERISTICS

[75] Inventor: Mario W. Medri, Millburn, N.J.

[73] Assignee: Consumer Products Corp., New York, N.Y.

[21] Appl. No.: 16,243

[22] Filed: Feb. 19, 1987

[51] Int. Cl.⁴ ............................ A61K 9/24; A61K 9/30
[52] U.S. Cl. ..................................... 424/441; 424/475; 424/479; 427/3
[58] Field of Search ...................... 424/441, 475, 479; 427/3

[56] References Cited

U.S. PATENT DOCUMENTS

| | | | |
|---|---|---|---|
| 4,423,086 | 12/1983 | Devos et al. | 424/479 X |
| 4,684,534 | 8/1987 | Valentine | 424/441 X |
| 4,716,041 | 12/1987 | Kjornaes et al. | 427/3 X |

*Primary Examiner*—Michael Lusignan
*Attorney, Agent, or Firm*—Kuhn and Muller

[57] ABSTRACT

A multiple-layer edible tablet is provided which contains a combination of different ingredients in separate layers wherein ingredients in one of the layers exhibits distinct organoleptic characteristics such as being perceived as cooling in contrast to the distinct organoleptic characteristics exhibited by the ingredients is another of the layers of the tablet such as being perceived as warming to enable the separate layers of the tablet to be identified when the tablet is being consumed by a user.

18 Claims, No Drawings

MULTIPLE-LAYER TABLET WITH CONTRASTING ORGANOLEPTIC CHARACTERISTICS

FIELD OF THE INVENTION

This invention relates to edible compositions in multiple-layer tablet form and, more particularly, to edible multiple-layer tablets containing different ingredients in separate layers having distinct organoleptic characteristics which can serve as a means for delivering a confection and/or medicament.

BACKGROUND OF THE INVENTION

It is known to prepare candy and pharmaceutical products in edible unit dosage form containing various combinations of ingredients to achieve particular characteristics. Generally, the combination of ingredients are premixed and then prepared in the desired form. In other instances, one or several of the ingredients will be covered with other ingredients to provide a two component dosage unit where the cover is used to delay the release of the covered ingredients in the mouth or digestive tract. State of the art, conventional tabletting equipment has also been used to prepare tablets containing various combinations of ingredients in single or multiple-layer tablet form. When multiple-layer tablets are formed, and it is desired to maintain the ingredients in separate layers, identification of this fact and of the distinct components is typically achieved by visual means, such as by adding different colored dyes. Candy flavoring or small amounts of topical additives having distinct organoleptic characteristics has also been used to achieve certain taste or flavor perception characteristics while the tablet is in the mouth. Frequently, this is done to mask undesirable taste characteristics of a drug being ingested, or to indicate some other distinct organoleptic characteristics.

Thus, there have been products made or suggested in the prior art containing combinations of ingredients in tablet or candy form, and even multiple-layer tablets with layers containing different compositions having means for visually distinguishing the same. However, to the best of our knowledge, there are no tablet or candy products wherein different solid or particulate ingredients are distinct and identifiable by the user as they are being ingested; nor are there multiple-layer tablets containing a combination of at least 2 different ingredients wherein each of said ingredients is in a separate layer suitable as a vehicle for other additives, including pharmaceuticals, medications, flavorings and the like, and which exhibit distinct and identifiable organoleptic characteristics until they are totally consumed.

SUMMARY OF THE INVENTION

It is an object of the present invention to provide multiple-layer tablets which are prepared from at least two different ingredients in separate and distinct layers of the tablet wherein the different ingredients are identifiable while being ingested in the oral cavity of a user.

It is a further object of the present invention to provide multiple-layer tablets containing different ingredients in distinct and separate layers which are identifiable by contrasting organoleptic characteristics while being ingested in the oral cavity of a user.

It is a still further object of the present invention to provide multiple-layer tablets containing two different ingredients in distinct and separate layers which are identifiable by one of the layers being an ingredient which imparts a sensation of cooling while dissolving on the tongue of a user and the other layer imparts a sensation, by contrast, of being non-cooling or warm while dissolving on the tongue of a user.

In accordance with the present invention there is provided a multiple-layer tablet containing a combination of ingredients in separate layers which are identifiable while being consumed, comprising:

a first layer containing an ingredient A which when dissolving on the tongue of a user is perceived as cooling until consumed; and a second layer containing an ingredient B which when dissolving on the tongue of a user is perceived in contrast to the ingredient A, as not cooling.

It has been found that multiple-layer tablets containing a combination of two particular ingredients which will be more fully described hereinafter, wherein said ingredients are not blended together prior to forming into a tablet as is generally done in tabletting practice, but are combined in a single tablet as distinct layers, when placed in the mouth of a user, impart distinct and identifiably contrasting organoleptic characteristics to a user which persist until the tablet is consumed. Preferably, the contrasting organoleptic characteristics are directed to one side of the tablet being perceived as cooling or being cold; and in contrast thereto, the other side of the tablet is perceived as being distinctly non-cooling, or even warm. To accomplish such surprising combination of contrasting, identifiable organoleptic characteristics in an edible tablet, a multiple-layer tablet in accordance with the invention is provided containing a layer comprised of an ingredient A which is a water-soluble, solid polyhydroxyl compound such as Sorbitol, and a separate, distinct layer of an ingredient B which may be a disaccharide such as Sucrose. Both ingredients are suitable for forming into tablets using conventional tabletting practices, and for use as a vehicle for tablet formulations that exhibit the contrasting organoleptic characteristics for identifying the separate layers of a multiple-layer tablet containing a combination thereof while being ingested by a user, until consumed.

DETAILED DESCRIPTION OF PREFERRED EMBODIMENTS

In accordance with the present invention the multiple-layer tablets containing a combination of at least two separate ingredients in distinct and identifiable layers is composed of a first layer containing an ingredient A and a further layer containing an ingredient B.

Suitable for use as ingredient A are polyhydroxyl compounds which are water-soluble and are available, or can be prepared, in a grade that can be formed into a tablet. Such suitable ingredients are edible and approved for such use. Illustrative of polyhydroxyl compounds suitable for use as ingredient A are Sorbitol, Mannitol, Xylatol and the like or mixtures thereof.

Suitable for use as ingredient B in the compositions of the invention are edible disaccharides which are water-soluble and are in a tabletting grade, or can be prepared in grade suitable for tabletting. Also suitable, are monosaccharides and polysaccharides which are edible, water-soluble and are available in a tabletting grade or can be prepared in a grade that can be formed into a tablet. Illustrative of suitable monosaccharides, disaccharides and polysaccharides are Sucrose, Lactose, Maltose, Glucose, Fructose, Dextrose and the like, or mixtures thereof.

The present invention provides an edible multiple-layer tablet composed of a combination of at least two different ingredients which enable tablets to deliver a wide variety of confections and/or medicaments while permitting the user to readily perceive and identify the distinct layers of the tablet. To accomplish such surprising advantages, one layer of the multiple-layer tablet contains an ingredient A based upon a polyhydroxyl compound or mixtures thereof as herein described which exhibits organoleptic characteristics distinct and identifiable in contrast to the organoleptic characteristics of ingredient B, the disaccharide, polysaccharide or mixture thereof, as herein described, which are contained in a second layer of the tablet. Thus, for example, when the tablet of the invention is placed in the mouth of a user, while dissolving on the tongue, there is imparted the distinct sensation of one side of the tablet being cool, or cold. In contrast thereto, when the other side of the tablet is dissolving on the tongue of the user, there is a distinct perception that the tablet is non-cooling, or even warmer.

While the amount of each of the ingredients A and B which can be used in combination in accordance with the invention can be varied, preferably, the relative amounts of ingredient A and ingredient B will be present in a weight ratio from about 30 to 70 to about 70 to 30 for any selected combination of such ingredients.

The particular combination of ingredients which are suitable for use in the invention may also be advantageously used as a vehicle for a great variety of other conventional ingredients to prepare formulations where a confection or medicament is desired. Conventional flavoring, colors, fruit acids, lubricants, binders, gliders, disintegrants, sweeteners as well as active pharmaceutical ingredients such as the type unti-tossive targeted to systemic and topical relief can be included with each of the ingredients A and/or B. Any combination and order of addition thereof can be used without affecting the perceived contrasting organoleptic characteristics of the combination of such ingredients while being dissolved in the users mouth.

While the type of such formulating ingredients that may be used is not critical, if the contrasting organoleptic characteristics exhibited by the combination of ingredient A and B is to be significantly perceived, the total amount of such additional ingredients should not be greater than the amount of ingredient A or ingredient B in each formulation. Preferably, the formulation in each of the layers of a two layer tablet will include common additional ingredients in amounts up to about 20 percent by weight and most preferably, not in excess of about 10 percent by weight. Included as a secondary or additional ingredients in any formulation may be the ingredient A or B subject to the same level of usage as other secondary ingredients.

In an alternate embodiment of the invention, the multiple-layer tablet may include a third separate and distinct layer which is, preferably, sandwiched between the other two layers. Where a third layer is included, preferably it is prepared from formulation including ingredient A or ingredient B, or the combination thereof. Such third layer, which is located intermediate the other two layers herein described, may be advantageously used as the delivering medium for active ingredients that are not compatible or stable in the presence of other active ingredients that may have been incorporated in the formulation of either or both of the other two layers.

As indicated, the novel multiple-layer tablets of the invention may be prepared by any conventional, state of the art, tabletting technique and ingredients A and B can be prepared in grades suitable for tabletting by means well known in the art.

The invention will become more clear when considered together with the following examples which are set forth as being merely illustrative of the invention and which are not intended, in any manner, to be limitative thereof. Unless otherwise indicated, all parts and percentages are by weight.

EXAMPLE 1

Two-layer tablet confections are prepared from the following formulation of ingredients. The tablets are prepared on a typical state of the art two-layer tabletting press using convention techniques.

| LAYER 1 | |
|---|---|
| | % |
| Sorbitol | 99.45 |
| Peppermint flavor | 0.22 |
| Magnesium stearate lubricant | 0.33 |

| LAYER 2 | |
|---|---|
| | % |
| Direct compression Sucrose (DI-PAC) | 99.38 |
| Peppermint flavor | 0.22 |
| Magnesium stearate lubricant | 0.40 |

The ingredients used in LAYER formulation 1 and LAYER formulation 2 are powders which are separately intimately admixed in a ribbon blender before each LAYER formulation is fed separately to the two-layer tabletting press. One gram of each LAYER formulation is used in preparing the multiple-layer tablet. The tabletting press is regulated to prepare two-layer, non-chewable tablets (yielding a hardness greater than 50 psig on edge; Strong-Cobb hardness tester).

The multiple-layer tablet confections have distinctly identifiable layers until consumed, with LAYER 1 being perceived as cooling when dissolving on the tongue of a user and LAYER 2 exhibiting non-cooling or warming characteristics.

EXAMPLE 2

Using the tabletting press and techniques of Example 1, two-layer tablet confections are prepared from the following formulation of ingredients:

TABLET 2A

| LAYER 1 | |
|---|---|
| | % |
| SORBITOL | 94.35 |
| SUCROSE (Direct Compression) | 5.00 |
| Natural orange flavor | 0.20 |
| Magnesium stearate lubricant | 0.45 |

LAYER 2

| | % |
|---|---|
| SUCROSE (Direct Compression) | 99.15 |
| Citric acid | 0.30 |
| Natural orange flavor | 0.15 |
| Magnesium stearate lubricant | 0.40 |

TABLET 2B

LAYER 1

| | % |
|---|---|
| Sorbitol | 88.95 |
| Mannitol | 10.00 |
| Color (FD&C Aluminum Lake) | 0.30 |
| Natural orange flavor | 0.25 |
| Magnesium stearate lubricant | 0.50 |

LAYER 2

| | % |
|---|---|
| Granulated Sucrose (2% corn syrup solids; added-80 ppm FD&C W.S. Dye) | 94.38 |
| Sorbitol | 5.00 |
| Natural orange flavor | 0.12 |
| Magnesium stearate lubricant | 0.50 |

Tablets 2A and 2B both exhibit distinct and identifiable layers until consumed, with LAYER 1 of each tablet exhibiting cooling characteristics when dissolving on the tongue of a user and LAYER 2 of each tablet exhibit non-cooling or warming characteristics.

EXAMPLE 3

Two-layer medicated tablets are prepared using the tabletting press and techniques of Example 1 from the following formulations:

TABLET 3A

LAYER 1

| | % |
|---|---|
| Sorbitol | 83.90 |
| Pharmaceutical ingredient* | 7.50 |
| Mannitol | 4.50 |
| Flavor** | 3.60 |
| Magnesium stearate lubricant | 0.50 |

*Dextro Methorphan Hydrobromide Adsorbate (DM) (10% purity, Hoffman La Roches) to deliver 7.5 mg of DM per each 2.0 gram tablet
**Menthol & Eucalyptous oil flavor blend, adsorbed in silica gel (1 part flavor and 2 part silica gel) to deliver 6.0 mg of menthol per 2.0 gram tablet.

LAYER 2

| | % |
|---|---|
| Sucrose (Direct Comp) | 93.48 |
| Fructose | 5.00 |
| Citric Acid | 0.50 |
| Color (FD&C Lake) | 0.30 |
| Orange flavor | 0.22 |
| Magnesium stearate lubricant | 0.50 |

TABLET 3B

LAYER 1

| | % |
|---|---|
| Sorbitol | 99.45 |
| Orange flavor | 0.22 |
| Magnesium stearate lubricant | 0.33 |

LAYER 2

| | % |
|---|---|
| Granulated sucrose (2% corn syrups solids) | 88.00 |
| Pharmaceutical ingredient* | 7.50 |
| Citric acid | 0.40 |
| Flavor** | 3.60 |
| Magnesium stearate lubricant | 0.50 |

*Dextro Methorphan Hydrobromide Adsorbate (DM)
**Menthol and Eucalyptous oil flavor blend, adsorbed in silica gel Tablets 3A and 3B exhibit distinct, contrasting organoleptic characteristics as well as known systemic and topical relief.

EXAMPLE 4

Using conventional three-layer tabletting apparatus and techniques, a series of three layer tablets are prepared from the following formulation of ingredients:

TABLET 4A

| LAYER 1 - the formulation of LAYER 1 in Example 1. | |
|---|---|
| LAYER 2 | |
| | % |
| Soribtol | 49.15 |
| Sucrose (Direct Comp) | 49.15 |
| Peppermint flavor | 0.20 |
| Magnesium stearate lubricant | 0.50 |
| LAYER 3 - the formulation of LAYER 2 in Example 1. | |

TABLET 4B

| LAYER 1 - the formulation of LAYER 1 for TABLET 2A in Example 2. | |
|---|---|
| LAYER 2 | |
| | % |
| Dextrose | 49.00 |
| Lactose | 26.80 |
| Sorbitol | 23.00 |
| Citric Acid | 0.45 |
| Natural Orange flavor | 0.25 |
| Magnesium stearate lubricant | 0.50 |
| LAYER 3 - The formulation of LAYER 2 for TABLET 2A in Example 2. | |

TABLET 4C

| LAYER 1 - The formulation of LAYER 1 for TABLET 2B in Example 2. | |
|---|---|
| LAYER 2 | |
| | % |
| Sorbitol | 49.15 |

-continued

| | |
|---|---|
| Granulated Sucrose (2% corn syrup solids) | 41.65 |
| Pharmaceutical ingredient* | 8.50 |
| Natural orange flavor | 0.22 |
| Magnesium stearate lubricant | 0.48 |

LAYER 3 - The formulation of LAYER 2 for TABLET 2B in Example 2

*Dextro Methorphan Hydromide Adsorbate (DM)

TABLETS 4A and 4B are prepared with LAYER formulations 1 and 3 as the outer layers and LAYER formulation 2 as the inner layer sandwiched between the outer layers. Tablets 4A and 4B exhibit distinct, contrasting organoleptic characteristics enabling the separate layers to be identified while being consumed.

What is claimed is:

1. A multiple-layer edible tablet containing a combination of ingredients which comprises:
    a non-chewable tablet having at least two separate layers including
    a first outer layer containing an ingredient A which when dissolving on the tongue of a user is perceived as cooling; and
    a second outer layer opposite side first layer containing an ingredient B which when dissolving on the tongue of a user is perceived, in contrast to the ingredient A, as not cooling;
    wherein said different ingredients in distinct layers are identifiable while said tablet is being consumed.

2. The multiple-layer tablet according to claim 1, wherein said ingredient A is a polyhydroxyl compound, and said ingredient B is a monosaccharide, disaccharide, polysaccharide or mixtures thereof.

3. The multiple-layer tablet according to claim 1, wherein said ingredient A and said ingredient B are present in said tablet in a ratio between about 30 to 70 and 70 to 30.

4. The multiple-layer tablet according to claim 2, wherein said ingredient A is Sorbitol, Mannitol, Xylatol, Moltitol or mixtures thereof.

5. The multiple-layer tablet according to claim 2, wherein said ingredient B is Sucrose, Lactose, Maltose, Glucose, Fructose, Dextrose or mixtures thereof.

6. The multiple-layer tablet according to claim 1, wherein said ingredient A is Sorbitol, Mannitol or mixtures thereof.

7. The multiple-layer tablet according to claim 6, wherein said ingredient B is Sucrose, Fructose or mixtures thereof.

8. The multiple-layer tablet according to claim 1, wherein said first layer comprises a composition containing at least about 50 percent by weight of said ingredient A.

9. The multiple-layer tablet according to claim 1, wherein said second layer comprises a composition containing at least about 50 percent by weight of said ingredient B.

10. The multiple-layer tablet according to claim 1, wherein said tablet has an edge hardness of at least about 50 psig (Strong-Cobb hardness), wherein said first layer consists essentially of a tabletting grade composition containing at least about 80 percent by weight of said ingredient A, and wherein said second layer consists essentially of a tabletting grade composition containing at least about 80 percent by weight of said ingredient B.

11. The multiple-layer tablet according to claim 1, which includes a separate layer sandwiched between said first and second layers.

12. A multiple-layer edible non-chewable tablet containing a combination of at least two different ingredients is separate, distinct layers on opposite sides thereof wherein each of said different ingredients exhibit contrasting organoleptic characteristics while said tablet is being consumed in the mouth of a user which provides means for distinctly identifying each of said ingredients.

13. The multiple-layer tablet according to claim 12, wherein one of said layers contains Sorbitol, Mannitol, Xylatol or mixture thereof and another of said layers contains Sucrose, Fructose, Dextrose or mixtures thereof.

14. The multiple-layer tablet according to claim 13, wherein one of said layers exhibits an organoleptic characteristic which is perceived as cooling while being consumed by dissolving on the tongue of a user and another of said layers exhibits an organoleptic characteristic which in contrast, is perceived as being non-cooling while being consumed by dissolving on the tongue of a user.

15. A method of preparing an edible tablet with a combination of ingredients wherein each of said ingredients are identifiable while said tablet is being consumed which comprises:
    forming a multiple-layer non-chewable edible tablet having at least two layers, said layers including
    a first outer layer containing a tablet formable ingredient A which is perceived as cooling when dissolving on the tongue of a user; and
    a second outer layer opposite said first layer containing a tablet formable ingredient B which is perceived in contrast to ingredient B, as not cooling when dissolving on the tongue of a user.

16. The method of preparing an edible tablet as claimed in claim 15, wherein said ingredient A is a polydroxyl compound, and said ingredient B is a monosaccharide, disaccharide, polysaccharide or mixtures thereof.

17. The method of preparing an edible tablet as claimed in claim 16, wherein said ingredient A and said ingredient B are present in said tablet in a ratio between about 30 to 70 and 70 to 30.

18. The method of preparing an edible tablet as claimed in claim 16, wherein said first layer consists essentially of at least about 80 percent by weight of said ingredient A and said second layer consists essentially of at least about 80 percent by weight of said ingredient B.

* * * * *

UNITED STATES PATENT AND TRADEMARK OFFICE
CERTIFICATE OF CORRECTION

PATENT NO. : 4,789,546
DATED : December 6, 1988
INVENTOR(S) : Mario W. Medri

It is certified that error appears in the above-identified patent and that said Letters Patent is hereby corrected as shown below:

Column 7, line 25, Claim 1, "side" should read -- said --.

Column 8, line 13, Claim 12, "is" should read -- in --.

Signed and Sealed this

Ninth Day of May, 1989

Attest:

DONALD J. QUIGG

Attesting Officer

Commissioner of Patents and Trademarks